US 7,022,678 B2

(12) United States Patent
Hurley et al.

(10) Patent No.: US 7,022,678 B2
(45) Date of Patent: Apr. 4, 2006

(54) PREGABALIN LACTOSE CONJUGATES

(75) Inventors: Timothy Robert Hurley, Ann Arbor, MI (US); Michael James Lovdahl, Ann Arbor, MI (US); Brian Tobias, Ann Arbor, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 93 days.

(21) Appl. No.: 10/058,903

(22) Filed: Jan. 28, 2002

(65) Prior Publication Data

US 2002/0187941 A1 Dec. 12, 2002

Related U.S. Application Data

(60) Provisional application No. 60/280,176, filed on Mar. 30, 2001.

(51) Int. Cl.
*A61K 31/7056* (2006.01)
*C07H 17/02* (2006.01)

(52) U.S. Cl. ............ 514/23; 514/649; 514/227.8; 514/231.5; 514/266.2; 514/300; 514/338; 514/43; 514/25; 514/561; 514/461; 514/557; 536/17.4; 536/4.1; 562/507; 560/122

(58) Field of Classification Search ........ 514/23, 514/43, 25, 561, 461, 557, 649, 227.8, 231.5, 514/266.2, 300, 338; 536/17.4, 4.1; 562/507; 560/122
See application file for complete search history.

(56) References Cited

U.S. PATENT DOCUMENTS

| | | | |
|---|---|---|---|
| 6,197,819 B1 | 3/2001 | Silverman et al. | 514/561 |
| 6,359,005 B1 * | 3/2002 | Pande | 514/561 |
| 6,488,964 B1 * | 12/2002 | Bruna et al. | 424/490 |
| 6,544,998 B1 * | 4/2003 | Mylari | 514/256 |

OTHER PUBLICATIONS

Wirth et al. "Maillard reaction of lactose and fluoxetine hydrochloride, a secondary amine", J. Pharm. Sci., vol. 87, No. 1, pp. 31-39, 1998.*

Maillard, "Chimie Organique—Action des acides amines sur les sucres; formation des melanoidines par voie methodique", *Comptes Rendus*, vol. 154, No. 2, 1912, pp. 66-68.

Colaco et al., "Pharmaceutical Formulation Instability and the Maillard Reaction", *Chimica Oggi*, vol. 14, 1996, pp. 32-37.

Wirth et al., "Maillard Reaction of Lactose and Fluoxetine Hydrochloride, a Secondary Amine", *J. Pharm. Sci.*, vol. 87, No. 1, 1998, pp. 31-39.

(Continued)

*Primary Examiner*—James O. Wilson
*Assistant Examiner*—Devesh Khare
(74) *Attorney, Agent, or Firm*—Charles W. Ashbrook; David R. Kurlandsky; Karen DeBenedictis

(57) ABSTRACT

In accordance with the present invention, there is provided pregabalin lactose conjugate compounds.

Figure 1:
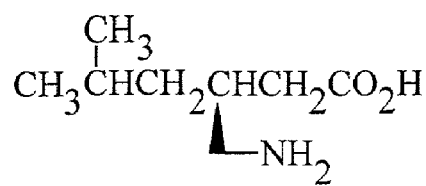
Figure 1:
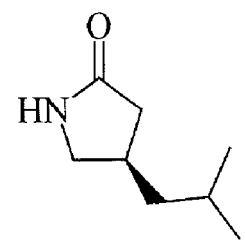
Figure 1:
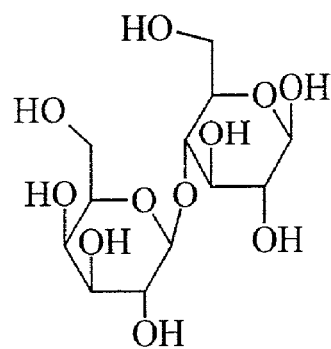
Figure 1:
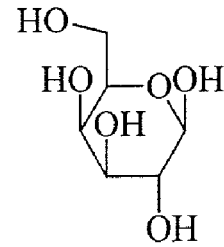
Figure 1:
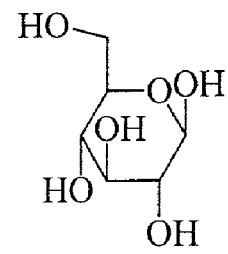

Also provided as part of the present invention is a novel method of central nervous system disorders or diseases including seizure disorders, pain, depression, anxiety, sleep disorders, consumptive disorders, psychosis, tardive dyskinesia, Huntington's disease, or Parkinson's disease in a subject by administering to the subject a pharmaceutically effective amount of a pregabalin lactose conjugate.

5 Claims, 3 Drawing Sheets

OTHER PUBLICATIONS

Hodge, "The Amadori Rearrangement", *Advances in Carbohydrate Chemnistry*, 1955, pp. 169-205.

Colaco C A L S, et al., "Pharmaceutical Formulation Instability and the Maillard Reaction", Chimica OGGI, Teknoscienze, Milano, IT, vol. 17, pp. 32-37 (Jul. 1996).

Field, M.J., et al., "Gabapentin and Pregabalin, But Not Morphine and Amitriptyline, Block Both Static and Dynamic Components of Mechanical Allodynia Induced by Streptozocin in the Rat", Pain, Elsevier Science Publishers, Amsterdam, NL, vol. 80, pp. 391-398 (1999).

Kumar, V., et al., "Maillard Reaction and Drug Stability", Maillard Reactions in Chemistry, Food and Health, p. 20-27 (1994).

Lovdahl, Michael J., et al., "Synthesis and characterization of pregabalin lactose conjugate degradation products", J. of Pharma and Biomed Analysis, vol. 28:5, p. 917-924 (Jun. 2002).

Maillard, L.C., "Action des acides amines sur les sucres; formation des melanoides par voie methodique", Comptes Rendus Des Seances De L'Academie Des Sciences, vol. 154, pp. 66-68 (1912).

Taylor, C.P., et al., "Potent and Sterospecific Anticonvulsand Activity of 3-Isobutyl Gaba Relates to In Vitro Bindings at a Novel Site Labeled by Tritiated Gabapentin", Epilepsy Research, Elsevier Science Publishers, Amsterdam, NL, vol. 14:1, pp. 11-15 (1993).

Wirth, D.D., et al., "Maillard reaction of lactose and fluoxetine hydrochloride, a secondary amine", Journal of Pharmaceutical Sciences, vol. 87:1, p. 31-39 (Jan. 1998).

* cited by examiner

Pregabalin

Pregabalin Lactam b-D-Lactose b-Galactose b-Glucose

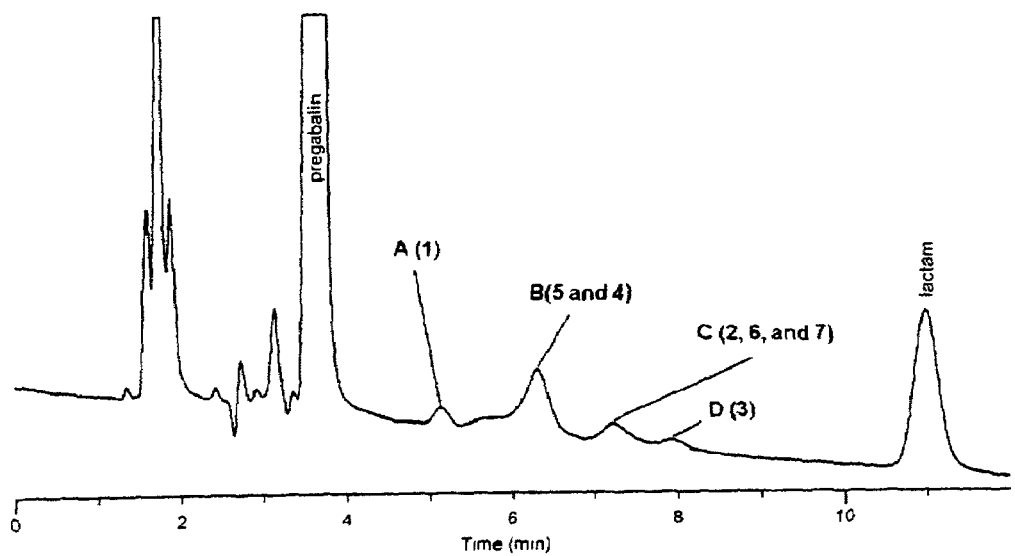
Figure 2. HPLC Chromatogram of Pregabalin 25-mg Capsule Stored at 40°C/75% RH for 6 Months (Original Method) HPLC Conditions: Column: Waters µ-Bondapak 10 µ C18, 300 × 3.9 mm ID; Mobile Phase: 550:350:100:1 $H_2O$:MeOH:$CH_2ON$:pH 7.0 Phosphate Buffer; Flow Rate: 1.0 mL/min; Detection: 210 nm; Temperature: Ambient; Compounds: as defined in Scheme 3

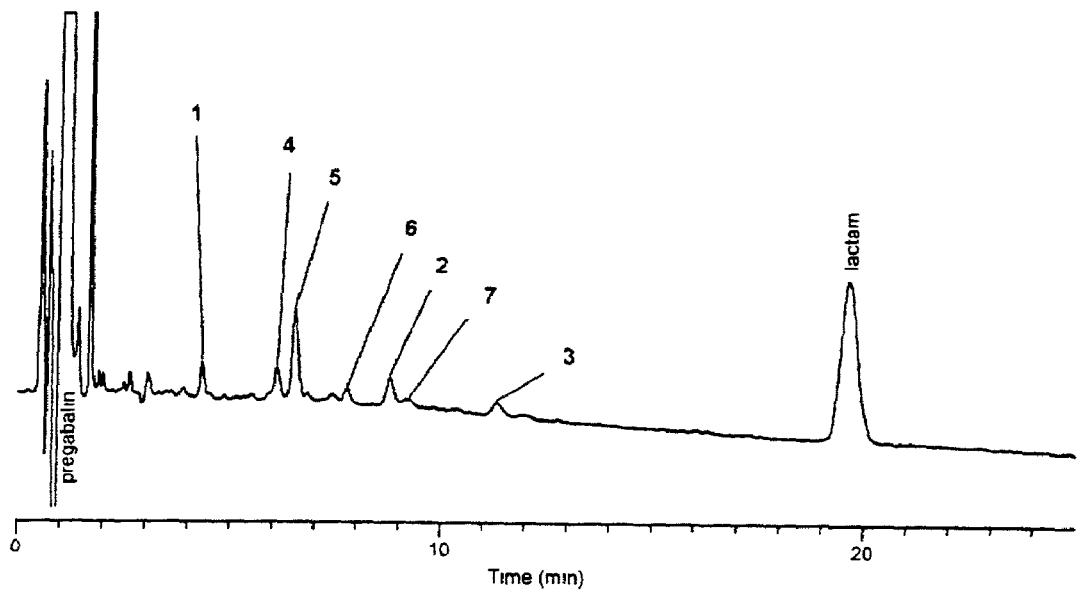
Figure 3. HPLC Chromatogram of Pregabalin 25-mg Capsules Stored at 40°C/75% RH for 6 Months (Modified Method) HPLC Conditions; Column: Phenomenex Luna C18 (2) 100 × 4.6 mm ID, 3 μ; Mobile Phase: 85:15 0.05% Formic Acid:CH$_3$CN; Flow Rate: 1.5 mL/min; Detection: 210 nm; Temperature: Ambient; Compounds: as defined in Scheme 3

PREGABALIN LACTOSE CONJUGATES

This application claims benefit of provisional application 60/280,176, filed Mar. 30, 2001.

TECHNICAL FIELD

The present invention relates to novel compounds that are analogs of glutamic acid and gamma-aminobutyric acid (GABA). More specifically, the analogs are conjugates of pregabalin and lactose and are useful in antiseizure therapy, and central nervous system disorders such as epilepsy, Huntington's disease, cerebral ischemia, Parkinson's disease, tardive dyskinesia, and spasticity. The compounds can also be used to treat depression, anxiety, pain, sleep disorders, consumptive disorders, and psychosis.

BACKGROUND OF THE INVENTION

Primary and secondary amines are known to form conjugates with lactose by undergoing a Maillard reaction (Maillard L. R., *Comptes Rendus*, 1912;154(2):66; Colaco C., Collett M., Roser B., *Chem Oggi*, 1996;14:32). Scheme 1 below shows the Maillard reaction of β-lactose with a primary amine. The product of this reaction is a simple glycosylamine, which is a combination of the lactose and the amine after a net loss of water. Maillard reaction products readily undergo an Amadori rearrangement to produce 1-amino-1-deoxy-2-ketoses, which exist in solution as a mixture of pyranose and furanose forms in equilibrium (see Scheme 2 below) (Wirth D., Baertschi S., Johnson R., et al., *J Pharm Sci,* 1998;87:31; Hodge J. E., *Advances in Carbohydrate Chemistry,* 1955:169–205). The seven degradants identified in formulated pregabalin were determined to be conjugates of pregabalin resulting from Maillard reactions. Heating pregabalin ((S)-3-(aminomethyl)-5-methyl hexanoic acid) (U.S. Pat. No. 6,197,819) in the presence of lactose formed significant quantities of these by-products. These compounds were isolated by preparative liquid chromatography and studied by mass spectrometry and NMR spectroscopy methods that led to the structural assignments (see Scheme 3 below). Four of these conjugates ((S)-4-isobutyl- 1-(2,3,4,5-tetrahydroxy-tetrahydro-pyran-2-ylmethyl)-pyrrolidin-2-one; (S)-4-isobutyl-1-(2,3,4,5-tetrahydroxy-tetrahydro-pyran-2-ylmethyl)-pyrrolidin-2-one; (S)-4-isobutyl-1-(2,3,4,5-tetrahydroxy-tetrahydro-pyran-2-ylmethyl)-pyrrolidin-2-one; and (S)-4-isobutyl-1-(2,3,4-trihydroxy-5-hydroxymethyl-tetrahydro-furan-2-ylmethyl)-pyrrolidin-2-one) are monoscaccarides, resulting from the Maillard reaction and Amardori rearrangement of pregabalin with either the galactose ((S)-4-isobutyl-1-(2,3,4,5-tetrahydroxy-teirahydro-pyran-2-ylmethl)-pyrrolidin-1-one and (S)-4-isobutyl-1-(2,3,4,5-tetrahydroxy-tetrahydro-pyran-2-ylmethyl)-pyrrolidin-2-one) or the glucose (S)-4-isobutyl-1-(2,3,4,5-tetrahydroxy-tetrahydro-pyran-2-ylmethyl)-pyrrolidin-2-one; and (S)-4-isobutyl-1-(2,3,4-trihydroxy-5-hydroxymethyl-tetrahydro-furan-2-ylmethyl)-pyrrolidin-2-one) moiety of lactose. The synthesis, isolation, and spectral characterization of seven by-products are described in this application.

SUMMARY OF THE INVENTION

In accordance with the present invention, there is provided pregabalin lactose conjugate compounds or pharmaceutically acceptable salts thereof.

In accordance with the present invention, there is provided compounds selected from:

(S)-1-[3,4-Dihydroxy-6-hydroxymethyl-5-(3,4,5-trihydroxymethyl-tetrahydro-pyran-2-yloxy)-tetrahydro-pyran-2-yl]-4-isobutyl-pyrrolidin-2-one;

(S)-4-Isobutyl-1-(2,3,4,5-tetrahydroxy-tetrahydro-pyran-2-ylmethyl)-pyrrolidin-2-one;

(S)-1-[2,3-Dihydroxy-5-hydroxymethyl-4-(3,4,5-trihydroxy-6-hydroxymethyl-tetrahydro-pyran-2-yloxy)-tetrahydro-furan-2-ylmethyl]-4-isobutyl-pyrrolidin-2-one;

(S)-4-Isobutyl-1-[2,3,5-trihydroxy-4-(3,4,5-trihydroxy-6-hydroxymethyl-tetrahydro-pyran-2-yloxy)-tetrahydro-pyran-2-ylmethyl]-pyrrolidin-2-one; and (S)-4-Isobutyl-1-(2,3,4-trihydroxy-5-hydroxymethyl-tetrahydro-furan-2-ylmethyl)-pyrrolidin-2-one.

The present invention also provides pharmaceutical compositions of the compounds selected from:

(S)-1-[3,4-Dihydroxy-6-hydroxymethyl-5-(3,4,5-trihydroxymethyl-tetrahydro-pyran-2-yloxy)-tetrahydro-pyran-2-yl]-4-isobutyl-pyrrolidin-2-one;

(S)-4-Isobutyl-1-(2,3,4,5-tetrahydroxy-tetrahydro-pyran-2-ylmethyl)-pyrrolidin-2-one;

(S)-1-[2,3-Dihydroxy-5-hydroxymethyl-4-(3,4,5-trihydroxy-6-hydroxymethyl-tetrahydro-pyran-2-yloxy)-tetrahydro-furan-2-ylmethyl]-4-isobutyl-pyrrolidin-2-one;

(S)-4-Isobutyl-1-[2,3,5-trihydroxy-4-(3,4,5-trihydroxy-6-hydroxymethyl-tetrahydro-pyran-2-yloxy)-tetrahydro-pyran-2-ylmethyl]-pyrrolidin-2-one; and (S)-4-Isobutyl-1-(2,3,4-trihydroxy-5-hydroxymethyl-tetrahydro-furan-2-ylmethyl)-pyrrolidin-2-one.

Also provided as part of the present invention is a novel method for treating central nervous system disorders or diseases including seizure disorders, pain, sleep disorders, consumptive disorders, depression, anxiety, psychosis, tardive dyskinesia, Huntington's or Parkinson's diseases in a subject by administering to the subject a pharmaceutically effective amount of a pregabalin lactose conjugate compound or a pharmaceutically acceptable salt thereof. The pregabalin lactose conjugate compound can be selected from:

(S)-1-[3,4-Dihydroxy-6-hydroxymethyl-5-(3,4,5-trihydroxymethyl-tetrahydro-pyran-2-yloxy)-tetrahydro-pyran-2-yl]-4-isobutyl-pyrrolidin-2-one;

(S)-4-Isobutyl-1-(2,3,4,5-tetrahydroxy-tetrahydro-pyran-2-ylmethyl)-pyrrolidin-2-one;

(S)-1-[2,3-Dihydroxy-5-hydroxymethyl-4-(3,4,5-trihydroxy-6-hydroxymethyl-tetrahydro-pyran-2-yloxy)-tetrahydro-furan-2-ylmethyl]-4-isobutyl-pyrrolidin-2-one;

(S)-4-Isobutyl-1-[2,3,5-trihydroxy-4-(3,4,5-trihydroxy-6-hydroxymethyl-tetrahydro-pyran-2-yloxy)-tetrahydro-pyran-2-ylmethyl]-pyrrolidin-2-one; and (S)-4-Isobutyl-1-(2,3,4-trihydroxy-5-hydroxymethyl-tetrahydro-furan-2-ylmethyl)-pyrrolidin-2-one.

Also, pharmaceutical compositions having a pregabalin lactose conjugate compound therein are disclosed.

BRIEF DESCRIPTION OF THE INVENTION

FIG. 1 illustrates the structures of pregabalin, pregabalin lactam, β-lactose, and β-lactose monomers (β-galactose and β-glucose);

FIG. 2 is an HPLC chromatogram of a pregabalin 25-mg capsule stored at 40° C./75% RH for 6 months; and FIG. 3 is an HPLC chromatogram of pregabalin 25-mg capsules stored at 40° C./75% RH for 6 months.

DETAILED DESCRIPTION OF THE INVENTION

In accordance with the present invention, there is provided a series of pregabalin-lactose conjugates which are useful in the treatment of central nervous system disorders or diseases, for example, as anticonvulsants, analgesics, antidepressants, anxiolytics, antipsychotics, antiseizure, antidyskinesics, or antisymptomatics for Huntington's or Parkinson's diseases.

In the long-term stability testing of formulated pregabalin capsules, four major peaks corresponding to degradation products were observed in high-pressure liquid chromatography (HPLC) chromatograms run. These products are described as degradation products formed by reaction of pregabalin with the excipient lactose (see FIG. 1) in pregabalin capsules. FIG. 2 shows an HPLC chromatograph of pregabalin 25 mg capsules, stored 4° C./75% RH for 6 months with the four peaks, Unknowns A, B, C, and D, labeled. Further investigation using a more specialized HPLC method revealed that Peaks B and C in the specifications and Test Methods arise from the coelution of multiple peaks. Peak B is the coelution of (S)-4-isobutyl-1-[2,3,5-trihydroxy-4-(3,4,5-trihydroxy-6-hydroxymethyl-tetrahydro-pyran-2-yloxy)-tetrahydro-pyran-2-ylmethyl]-pyrrolidin-2-one and (S)-1-[2,3-dihydroxy-5-hydroxymethyl-4-(3,4,5-trihydroxy-6-hydroxymethyl-tetrahydro-pyran-2-yloxy)-tetrahydro-furan-2-ylmethyl]-4-isobutyl-pyrrolidin-2-one. Peak C is the coelution of ((S)-4-isobutyl-1-(2,3,4,5-tetrahydroxy-tetrahydro-pyran-2-ylmethyl)-pyrrolidin-2-one; (S)-4-isobutyl-1-(2,3,4,5-tetrahydroxy-tetrahydro-pyran-2-ylmethyl) -pyrrolidin-2-one; and (S)-4-isobutyl-1-(2,3,4-trihydroxy-5-hydroxymethyl-tetrahydro-furan-2-ylmethyl)-pyrrolidin-2-one). FIG. 3 shows an HPLC chromatogram of pregabalin 25-mg capsules (6 months at 40° C./75% RH) using a specialized HPLC method with seven lactose conjugates labeled ((S)-1-[3,4-dihydroxy-6-hydroxymethyl-5-(3,4,5-trihydroxy-6-hydroxymethyl-tetrahydro-pyran-2-yloxy)-tetrahydro-pyran-2-yl]-4-isobutyl-pyrrolidin-2-one; (S)-4-isobutyl-1-(2,3,4,5-tetrahydroxy-tetrahydro-pyran-2-ylmethyl)-pyrrolidin-2-one; (S)-4-isobutyl-1-[2,3,5-trihydroxy-4-(3,4,5-trihydroxy-6-hydroxymethyl-tetrahydro-pyran-2-yloxy)-tetrahydro-pyran-2-ylmethyl]-pyrrolidin-2-one; (S)-1-[2,3-dihydroxy-5-hydroxymethyl-4-(3,4,5-trihydroxy-6-hydroxymethyl-tetrahydro-pyran-2-yloxy)-tetrahydro-furan-2-ylmethyl]-4-isobutyl-pyrrolidin-2-one; (S)-4-isobutyl-1-(2,3,4,5-tetrahydroxy-tetrahydro-pyran-2-ylmethyl)-pyrrolidin-2-one; (S)-4-isobutyl-1-(2,3,4,5-tetrahydroxy-tetrahydro-pyran-2-ylmethyl)-pyrrolidin-2-one; and (S)-4-isobutyl-1-(2,3,4-trihydroxy-5-hydroxymethyl-tetrahydro-furan-2-ylmethyl)-pyrrolidin-2-one).

The compounds include:

(S)-1-[3,4-Dihydroxy-6-hydroxymethyl-5-(3,4,5-trihydroxymethyl-tetrahydro-pyran-2-yloxy)-tetrahydro-pyran-2-yl]-4-isobutyl-pyrrolidin-2-one;

(S)-4-Isobutyl-1-(2,3,4,5-tetrahydroxy-tetrahydro-pyran-2-ylmethyl)-pyrrolidin-2-one;

(S)-1-[2,3-Dihydroxy-5-hydroxymethyl-4-(3,4,5-trihydroxy-6-hydroxymethyl-tetrahydro-pyran-2-yloxy)-tetrahydro-furan-2-ylmethyl]-4-isobutyl-pyrrolidin-2-one;

(S)-4-Isobutyl-1-[2,3,5-trihydroxy-4-(3,4,5-trihydroxy-6-hydroxymethyl-tetrahydro-pyran-2-yloxy)-tetrahydro-pyran-2-ylmethyl]-pyrrolidin-2-one; and (S)-4-Isobutyl-1-(2,3,4-trihydroxy-5-hydroxymethyl-tetrahydro-furan-2 ylmethyl)-pyrrolidin-2-one.

The compounds have the structures:

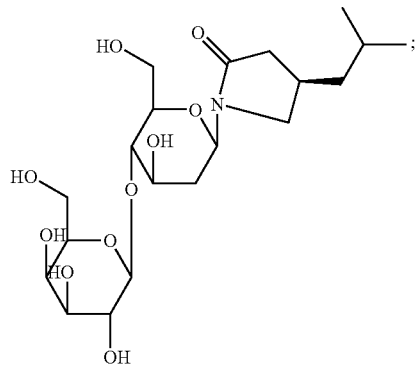

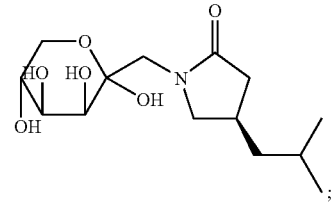

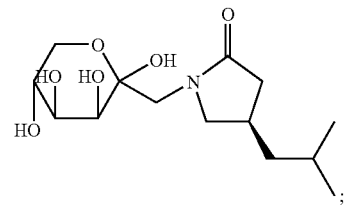

-continued
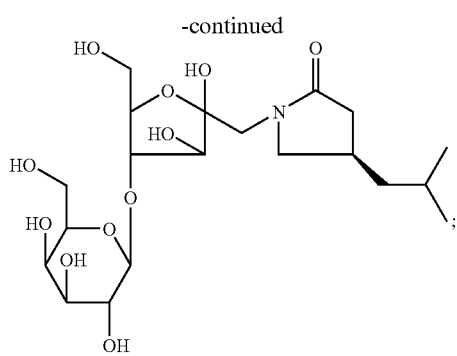
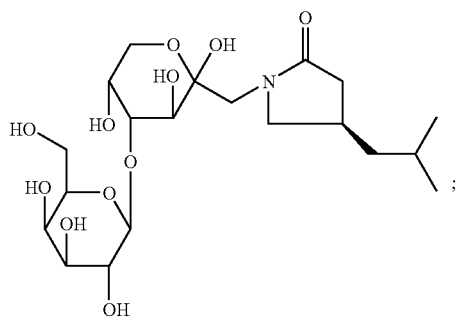
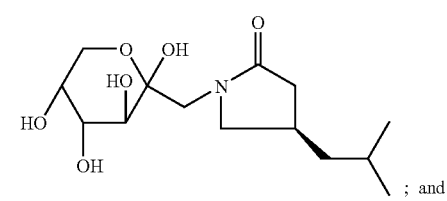
; and
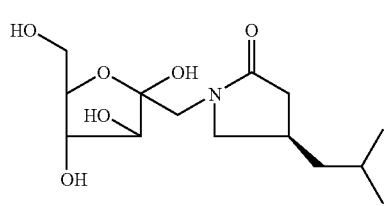
General Synthesis:
Compounds of the present invention can be prepared by applying synthetic methodology known in the art and synthetic methodology outlined in Schemes 1 to 3 set forth below.
Scheme 1
Maillard Reaction of β-Lactose With a Primary Amine
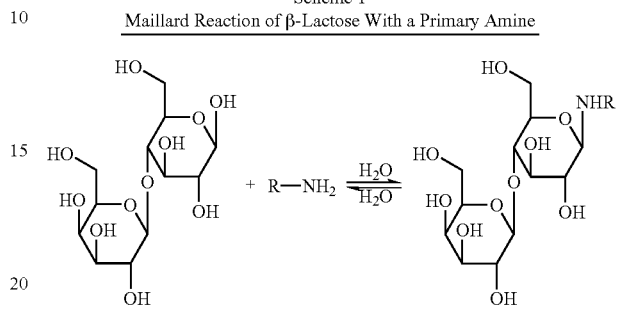
Scheme 2
Amadori Arrangement
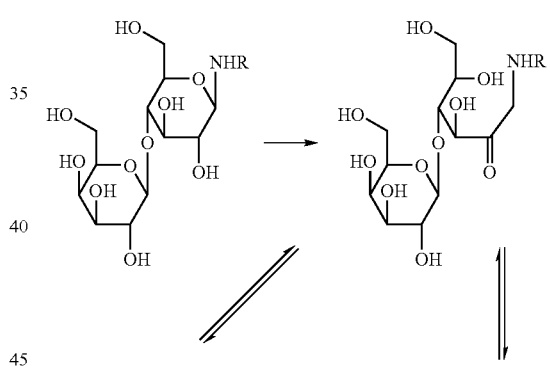
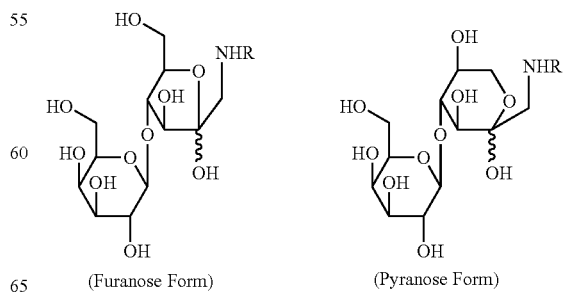
(Furanose Form)   (Pyranose Form)

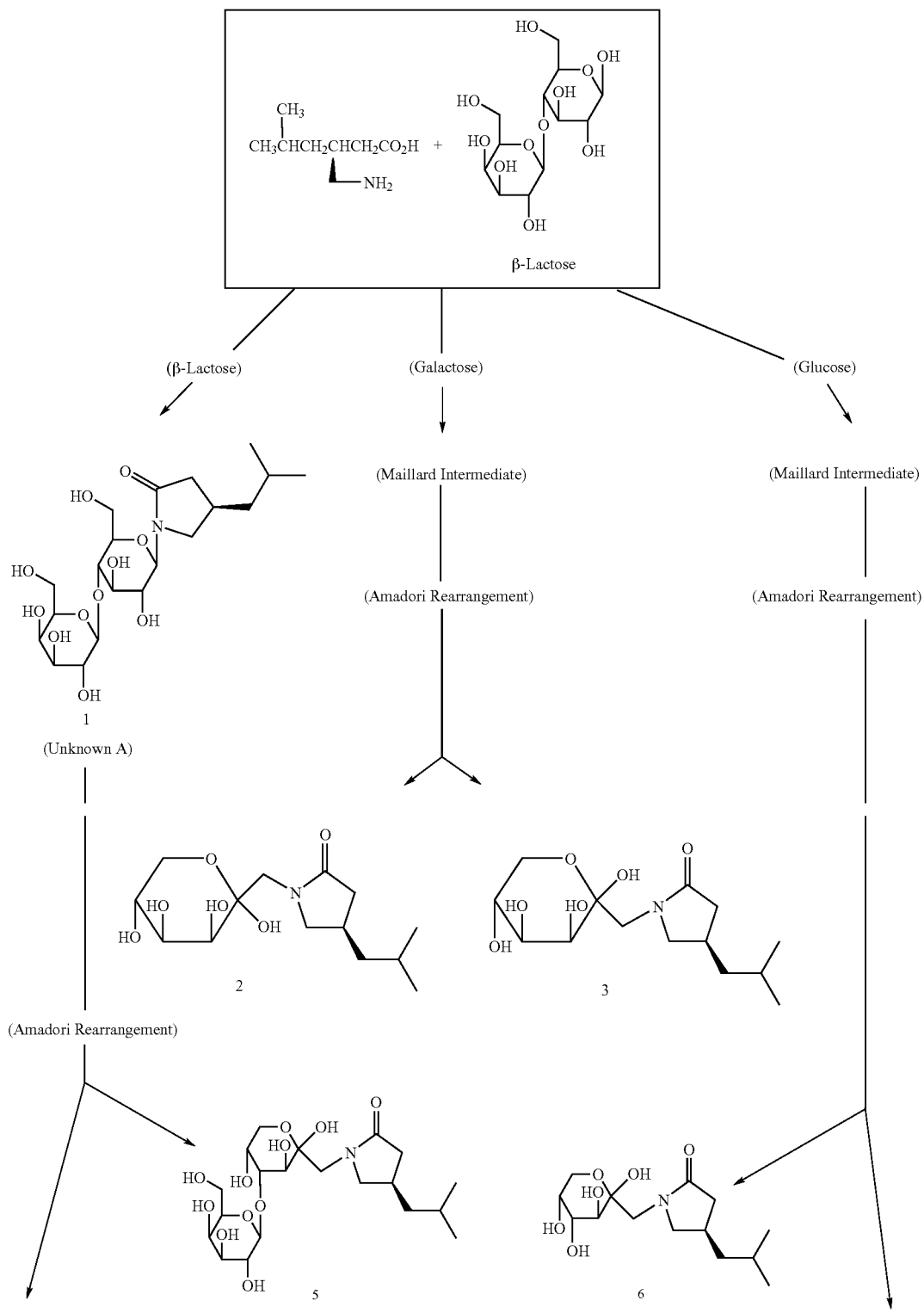
Scheme 3
Lactose Conjugates of Pregabalin

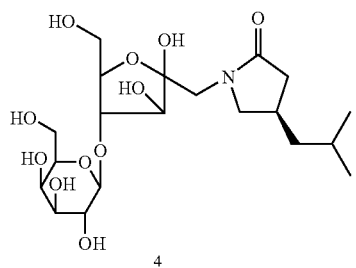

4

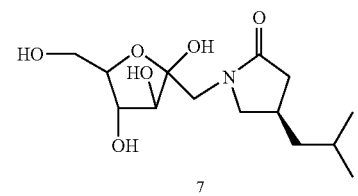

7

The pregabalin lactose conjugates are useful agents for the treatment of central nervous system disorders and diseases including seizures, pain, depression, anxiety, sleep disorders, consumptive disorders, psychosis, tardive dyskinesia, Huntington's disease, and Parkinson's disease.

A pregabalin lactose conjugate compound can be administered to a patient (e.g., a human) alone or in conjunction with (before, along with, or subsequent to) one or more other pregabalin lactose derivative compounds or another agent to be administered.

The compounds of the present invention can be prepared and administered in a wide variety of routes of administration such as parenteral, oral, topical, rectal, inhalation, and the like. Formulations will vary according to the route of administration selected. Examples are oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. The dosage forms described below may comprise as the active component, a compound selected from:

(S)-1-[3,4-Dihydroxy-6-hydroxymethyl-5-(3,4,5-trihydroxymethyl-tetrahydro-pyran-2-yloxy)-tetrahydro-pyran-2-yl]-4-isobutyl-pyrrolidin-2-one;

(S)-4-Isobutyl-1-(2,3,4,5-tetrahydroxy-tetrahydro-pyran-2-ylmethyl)-pyrrolidin-2-one;

(S)-1-[2,3-Dihydroxy-5-hydroxymethyl-4-(3,4,5-trihydroxy-6-hydroxymethyl-tetrahydro-pyran-2-yloxy)-tetrahydro-furan-2-ylmethyl]-4-isobutyl-pyrrolidin-2-one;

(S)-4-Isobutyl-1-[2,3,5-trihydroxy-4-(3,4,5-trihydroxy-6-hydroxymethyl-tetrahydro-pyran-2-yloxy)-tetrahydro-pyran-2-ylmethyl]-pyrrolidin-2-one; and (S)-4-Isobutyl-1-(2,3,4-trihydroxy-5-hydroxymethyl-tetrahydro-furan-2-ylmethyl)-pyrrolidin-2-one; or a corresponding pharmaceutically acceptable salt of: (S)-1-[3,4-Dihydroxy-6-hydroxymethyl-5-(3,4,5-trihydroxymethyl-tetrahydro-pyran-2-yloxy)-tetrahydro-pyran-2-yl]-4-isobutyl-pyrrolidin-2-one;

(S)-4-Isobutyl-1-(2,3,4,5-tetrahydroxy-tetrahydro-pyran-2-ylmethyl)-pyrrolidin-2-one;

(S)-1-[2,3-Dihydroxy-5-hydroxymethyl-4-(3,4,5-trihydroxy-6-hydroxymethyl-tetrahydro-pyran-2-yloxy)-tetrahydro-furan-2-ylmethyl]-4-isobutyl-pyrrolidin-2-one;

(S)-4-Isobutyl-1-[2,3,5-trihydroxy-4-(3,4,5-trihydroxy-6-hydroxymethyl-tetrahydro-pyran-2-yloxy)-tetrahydro-pyran-2-ylmethyl]-pyrrolidin-2-one; and (S)-4-Isobutyl-1-(2,3,4-trihydroxy-5-hydroxymethyl-tetrahydro-furan-2-ylmethyl)-pyrrolidin-2-one.

The symbol "—" means a bond.

The term "subject" means all animals including humans. Examples of patients include humans, cows, dogs, cats, goats, sheep, and pigs.

The compound of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R(D) or S(L) configuration. The present invention includes all enantiomeric and epimeric forms as well as the appropriate mixtures thereof.

The compounds of the present invention are capable of further forming both pharmaceutically acceptable analogs comprising salts, esters, amides, and prodrugs. As used herein, the term "pharmaceutically acceptable salts, esters, amides, and prodrugs" refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively nontoxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed and including, but not limited to, acid addition and/or base salts, solvents, and N-oxides of a pregabalin lactose conjugate compound. This invention also provides pharmaceutical formulations comprising a pregabalin lactose conjugate compound together with a pharmaceutically acceptable carrier, diluent, or excipient therefor. All of these forms are within the present invention.

Pharmaceutically acceptable acid addition salts of the pregabalin lactose conjugate compounds include salts derived from inorganic acids such as hydrochloric, nitric, phosphoric, sulfuric, hydrobromic, hydriodic, phosphorus, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are the salts of amino acids such as arginate, gluconate, galacturonate, and the like; see, for example, Berge et al., "Pharmaceutical Salts," *J. of Pharmaceutical Science,* 1977;66:1–19.

The acid addition salts of the basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metal hydroxides, or of organic amines. Examples of metals used as cations are sodium, potassium, magnesium, calcium, and the like. Examples of suitable amines are N,N'-dibenzylethylenediamine, chloroprocaine, choline, diethanolamine, ethylenediamine, N-methylglucamine, and procaine (see, for example, Berge et al., supra., 1977).

The base addition salts of acidic compounds are prepared by contacting the free acid form with a sufficient amount of the desired base to produce the salt in the conventional manner. The free acid form may be regenerated by contacting the salt form with an acid and isolating the free acid in a conventional manner. The free acid forms differ from their respective salt forms somewhat in certain physical properties such as solubility in polar solvents, but otherwise the salts are equivalent to their respective free acid for purposes of the present invention.

Examples of pharmaceutically acceptable, nontoxic esters of the compounds of this invention include $C_1$–$C_6$alkyl esters wherein the alkyl group is a straight or branched chain. Acceptable esters also include $C_5$–$C_7$cycloalkyl esters as well as arylalkyl esters such as, but not limited to, benzyl. $C_1$–$C_4$alkyl esters are preferred. Esters of the compounds of the present invention may be prepared according to conventional methods.

Examples of pharmaceutically acceptable, nontoxic amides of the compounds of this invention include amides derived from ammonia, primary $C_1$–$C_6$alkyl amines and secondary $C_1$–$C_6$dialkyl amines wherein the alkyl groups are straight or branched chain. In the case of secondary amines, the amine may also be in the form of a 5- or 6-membered heterocycle containing one nitrogen atom. Amides derived from ammonia, $C_1$–$C_3$alkyl primary amines, and $C_1$–$C_2$dialkyl secondary amines are preferred. Amides of the compounds of the invention may be prepared according to conventional methods.

The term "prodrug" refers to compounds that are rapidly transformed in vivo to yield the parent compound of the above Formulae, for example, by hydrolysis in blood. A thorough discussion is provided in T. Higuchi and V. Stella, "Pro-drugs as Novel Delivery Systems," Vol 14 of the A.C.S. Symposium Series, and in *Bioreversible Carriers in Drug Design,* ed. Edward B. Roche, American Pharmaceutical Association and Pergamon Press, 1987, both of which are incorporated herein by reference. In general, a prodrug is a drug which has been chemically modified and may be biologically inactive at its site of action, but which may be degraded or modified by one or more enzymatic or other in vivo processes to the parent bioactive form.

A therapeutically effective amount is an amount of a pregabalin lactose conjugate compound, that when administered to a patient, ameliorates a symptom of the disease.

The pregabalin lactose conjugate compound or a pharmaceutically acceptable salt of any of the foregoing, can be administered in accordance with the present inventive method by any suitable route. Suitable routes of administration include systemic, such as orally or by injection and topical.

One skilled in the art will appreciate that suitable methods of administering a pregabalin lactose conjugate, which is useful in the present inventive method, are available. Although more than one route can be used to administer a particular pregabalin lactose conjugate compound, a particular route can provide a more immediate and more effective reaction than another route. Accordingly, the described routes of administration are merely exemplary and are in no way limiting.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier can be a finely divided solid which is in a mixture with the finely divided active component.

In tablets, the active component can be mixed with the carrier having the necessary binding properties in suitable proportions and compacted in the shape and size desired.

The powders and tablets preferably contain from 5% or 10% to about 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted, and the active component can be dispersed homogeneously therein, as by stirring. The molten homogenous mixture can be then poured into convenient sized molds, allowed to cool, and thereby to solidify.

Liquid form preparations include solutions, suspensions, and emulsions, for example, water or water propylene glycol solutions. For parenteral injection, liquid preparations can be formulated in solution in a pharmaceutically acceptable carrier, such as, aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water or another suitable carrier with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The dose administered to an animal, particularly a human, in accordance with the present invention should be sufficient to effect the desired response in the animal over a reasonable time frame. One skilled in the art will recognize that dosage will depend upon a variety of factors, including the strength of the particular pregabalin lactose conjugate compound employed, the age, species, condition or disease state, and body weight of the animal, as well as the amount of the retina about to be affected or actually affected by retinopathy. The size of the dose also will be determined by the route, timing, and frequency of administration as well as the existence, nature, and extent of any adverse side effects that might accompany the administration of a particular pregabalin lactose conjugate compound and the desired physiological effect. It will be appreciated by one of ordinary skill in the art that various conditions or disease state, in particular, chronic conditions or disease states, may require prolonged treatment involving multiple administrations.

In therapeutic use as agents for the treatment of central nervous system disorders and central nervous system diseases such as anxiety and pain, the compounds utilized in the pharmaceutical methods of this invention can be administered at an initial dosage of about 0.01 mg to about 200 mg/kg daily. A daily dose range of about 0.01 mg to about 50 mg/kg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

The following nonlimiting examples illustrate preferred methods for preparing compounds of the invention.

EXPERIMENTAL

Materials

Pregabalin was used as received from Pfizer Global Research and Development (Ann Arbor, Mich.). All other reagents and solvents were of analytical or HPLC grade. The solid chemicals were purchased from E. Merck (Darmnstadt, Germany) and the solvents from Mallinckrodt (Paris, Ky.).

Apparatus

The mass spectra were run on a Micromass Quattro II (Manchester, England) triple quadrapole mass spectrometer using electrospray ionization. Nuclear Magnetic Resonance (NMR) experiments were performed at ambient temperature on a Varian INOVA 400 (Palo Alto, Calif.) operating at 400 MHz for $^1$H-NMR and 100 MHz for $^{13}$C—NMR. Analytical scale chromatography was performed using a Perkin-Elmer (Norwalk, Conn.) Series 200 LC pump, Series 200 autosampler, and LC-235 diode array detector. Analytical separations were performed on a YMC ODS-AQ column, 100×2.1 mm, 5-µm particle size at 30° C. Mobile phase consisted of 15 parts acetonitrile, 10 parts methanol, and 75 parts 0.1% formic acid, which was delivered at a rate of 0.25 mL/min. Preparative scale chromatography was performed using a Varian Dynamax SD-1 solvent delivery system, SD-300 sample introduction pump, UV-1 detector, and an Isco (Lincoln, Nebr.) Foxy 200 fraction collector. Mobile phase was delivered at 25 mL/min through a Dynamax C18 250×41 mm, 8-µm column at ambient temperature.

Synthesis of Crude Pregabalin Lactose Conjugates

Pregabalin (0.8 g) and lactose (3.8 g) were dissolved in 5 mL of water with stirring and heat. The solution was then heated at 90° C. in an open Pyrex™ beaker using a heating block overnight. The resulting solid was then redissolved in approximately 20 mL of isopropyl alcohol by sonicating and heating. Forty milliliters of acetonitrile were added to this solution. The resulting solid was subjected to preparative scale reversed-phase chromatography.

Purification of Pregabalin Lactose Conjugates

The solid material obtained above was subjected to reversed-phase preparative chromatography by injecting 20 mL of a saturated solution in mobile phase onto the preparative system described in Table 1. Fifty milliliter fractions were collected beginning at 150 mL of retention. Fractions were analyzed by HPLC, and those corresponding to the peaks of interest were pooled. The pooled fractions were concentrated on a rotoevaporator to remove the acetonitrile and methanol prior to lyophilization.

LC/MS Experiments

Sample introduction and ionization was by electrospray ionization (ESI) in the positive ion detection mode. Source cone voltage of 20 V, capillary voltage of 3.5 KV, and a source temperature of 90° C. with drying gas set to 450 L/hour and nebulizing gas set to 35 L/hour were the ionization parameters. The initial scan rate was 2.0 seconds/decade over a mass range of 50 to 1250 amu. Scan data was acquired using MassLynx multitasking operating system, Version 3.2. The mass spectrometer was operated in MS/MS mode using argon as the collision gas at an indicated gas cell pressure of $1.5 \times 10^{-3}$ torr and collision energy of 25 eV. Sample solutions were monitored in full scan, product, precursor, and neutral loss scanning modes.

NMR Experiments

NMR experiments were performed at ambient temperature on a Varian INOVA 400 (Palo Alto, Calif.) operating at 400 MHz for $^1$H-NMR and 100 MHz for $^{13}$C-NMR. All samples were run in $D_2O$. Typical sample size was 10 to 15 mg. All spectra referenced to residual HDO at 4.63 ppm. Typically, $^1$H, $^{13}$C, APT (Attached Proton Test), gCOSY, gHMQC, gHMBC, and TOCSY NMR data were obtained for each conjugate.

EXAMPLE 1

(S)-1-[3,4-Dihydroxy-6-hydroxymethyl-5-(3,4,5-trihydroxymethyl-6-hydroxymethyl-tetrahydro-pyran-2-yloxy)-tetrahydro-pyran-2-yl]-4-isobutyl-pyrrolidin-2-one Isolated (S)-1-[3,4-dihydroxy-6-hydroxymethyl-5-(3,4,5-trihydroxymethyl-6-hydroxymethyl-tetrahydro-pyran-2-yloxy)-tetrahydro-pyran-2-yl]-4-isobutyl-pyrrolidin-2-one, Lot P was 79% pure by HPLC area normalization. The relative response factor determined for (S)-1-[3,4-dihydroxy-6-hydroxymethyl-5-(3,4,5-trihydroxy-6-hydroxymethyl-tetrahydro-pyran-2-yloxy)-tetrahydro-pyran-2-yl]-4-isobutyl-pyrrolidin-2-one versus pregabalin in the capsule method is 15.9. The relative response factor, shown in Table 2, is the ratio of the response factors determined for pregabalin and for the conjugate in the same HPLC system. The response factor for each component is the area response divided by the concentration of analyte. The relative response factor is determined in the following equation:

$$\text{Relative Response Factor}(RRF) = \frac{RF_{conjugate}}{RF_{pregabalin}}$$

where:

$Rf_{conjugate}$=Area response of conjugate divided by concentration of conjugate.

$Rf_{pregabalin}$=Area response of pregabalin divided by concentration of pregabalin.

The anomeric protons for the galactose (4.28 ppm) and glucose (4.87 ppm) moieties of lactose are observed in the proton spectrum. The anomeric carbons for the galactose (102.9 ppm) and glucose (80.3 ppm) moieties are also observed with their expected multiplicities. The profile of carbon signals in the glucose moiety (80.3, 69.5, 75.3, 77.6, 76.9, and 59.9 ppm for $C_1$–$C_6$, respectively) is consistent with the β-anomer (Breitmaier E., Voelter W., *Carbon*-13 *NMR Spectroscopy*, 1990:379). The chemical shifts arising from the pregabalin moiety in the proton (0.7–3.6 ppm) and carbon (20–50 ppm, aliphatic) spectra are consistent with the lactam (closed-ring) form of the molecule. The ion at m/z 466 in the mass spectrum (ESI+) of ((S)-1-[3,4-dihydroxy-6-hydroxymethyl-5-(3,4,5-trihydroxy-6-hydroxymethyl-tetrahydro-pyran-2-yloxy)-tetrahydro-pyran-2-yl]-4-isobutyl-pyrrolidin-2-one arises from the protonated molecule. The mass of m/z 465 is consistent with the formula for ((S)-1-[3,4-dihydroxy-6-hydroxymethyl-5-(3,4,5-trihydroxy-6-hydroxymethyl-tetrahydro-pyran-2-yloxy)-tetrahydro-pyran-2-yl]-4-isobutyl-pyrrolidin-2-one, $C_{20}H_{35}NO_{11}$. The product ion spectrum is consistent with the proposed structure. (S)-1-[3,4-dihydroxy-6-hydroxymethyl-5-(3,4,5-trihydroxy-6-hydroxymethyl-tetrahydro-pyran-2-yloxy)-tetrahydro-pyran-2-yl]-4-isobutyl-pyrrolidin-2-one is the lactam form of the glycosylamine formed by the Maillard reaction of pregabalin and lactose (β-anomer). Since the Maillard reaction only occurs with reducing carbohydrates and amines (primary or secondary) (Maillard L. R., supra., 1912; Colaco C., Collett M., Roser B., supra., 1996; Wirth D., Baertschi S., Johnson R., et al., supra., 1998), it is assumed that lactam formation in pregabalin conjugates follows the initial Maillard reaction.

EXAMPLE 2

(S)-1-[2,3-Dihydroxy-5-hydroxymethyl-4-(3,4,5-trihydroxy-6-hydroxymethyl-tetrahydro-pyran-2-yloxy)-tetrahydro-furan-2-ylmethyl]-4-isobutyl-pyrrolidin-2-one and (S)-4-Isobutyl-1-[2,3,5-trihydroxy-4-(3,4,5-trihydroxy-6-hydroxymethyl-tetrahydro-pyran-2-yloxy)-tetrahydro-pyran-2-ylmethyl]-pyrrolidin-2-one in a 3:1 "Mixture"

These compounds were isolated in a 3:1 mixture. This mixture of isomers (furanose, pyranose), as a 3:1 mixture, is identical to the single peak referred to as Unknown B in the method for pregabalin capsules. The relative response factor for mixture versus pregabalin is 20.2. The anomeric galactosyl protons for (S)-1-[2,3-dihydroxy-5-hydroxymethyl-4-(3,4,5-trihydroxy-6-hydroxymethyl-tetrahydro-pyran-2-yloxy)-tetrahydro-furan-2-ylmethyl]-4-isobutyl-pyrrolidin-2-one and (S)-4-isobutyl-1-[2,3,5-trihydroxy-4-(3,4,5-trihydroxy-6-hydroxymethyl-tetrahydro-pyran-2-yloxy)-tetrahydro-pyran-2-ylmethyl]-pyrrolidin-2-one are observed at 4.3 and 4.4 ppm in the proton spectrum. No other anomeric protons are observed. In the carbon spectrum, nonproton bearing carbons are observed at 98.6 and 102.4 ppm, in addition to the galactose anomeric carbons at 100.9 and 103.4 ppm (1 proton attached). The profile of carbon signals in the arabinosyl moiety of (S)-1-[2,3-dihydroxy-5-hydroxymethyl-4-(3,4,5-trihydroxy-6-hydroxymethyl-tetrahydro-pyran-2-yloxy)-tetrahydro-furan-2-ylmethyl]-4-isobutyl-pyrrolidin-2-one (102.4, 76.5, 84.3, 80.0, and 62.7 ppm for $C_1$–$C_5$, respectively) is consistent with the β-furanose form. The profile for the arabinosyl moiety of (S)-4-isobutyl-1-[2,3,5-trihydroxy-4-(3,4,5-trihydroxy-6-hydroxymethyl-tetrahydro-pyran-2-yloxy)-tetrahydro-pyran-2-ylmethyl]-pyrrolidin-2-one (98.6, 67.7, 77.3, 66.7, and 63.1 ppm for $C_1$–$C_5$, respectively) is consistent with the β-pyranose form (Breitmaier E., Voelter W., supra., 1990). The chemical shifts arising from the pregabalin moiety in the proton (0.7–3.6 ppm) and carbon (20–60 ppm, aliphatic) spectra are consistent with the lactam (closed-ring) form of the molecule. The ion at m/z 466 in the mass spectrum (ESI+) of mixture arises from the protonated molecule. The mass of m/z 465 is consistent with the formula for mixture, $C_{20}H_{35}NO_{11}$. The product ion spectrum is, consistent with the proposed structure.

EXAMPLE 3

(S)-4-Isobutyl-1-(2,3,4,5-tetrahydroxy-tetrahydro-pyran-2-ylmethyl)-pyrrolidin-2-one Isolated (S)-4-isobutyl-1-(2,3,4,5-tetrahydroxy-tetrahydro-pyran-2-ylmethyl)-pyrrolidin-2-one, Lot P was 70% pure by HPLC area normalization. The relative response factor determined for (S)-4-isobutyl-1-2,3,4,5-tetrahydroxy-tetrahydro-pyran-2-ylmethyl)-pyrrolidin-2-one versus pregabalin in the method is 28.1. Both anomeric protons are missing from the proton spectrum, and a nonproton bearing carbon at 98.6 ppm is observed in the $^{13}C$ spectrum. In the carbon spectrum, the profile of signals in the lyxose moiety (98.6, 70.6, 70.7, 66.2, and 62.4 ppm for $C_1$–$C_5$, respectively) is consistant with the α-anomer (pyranose form) (Breitmaier E., Voelter W., supra., 1990). The chemical shifts arising from the pregabalin moiety in the proton (0.7–3.6 ppm) and carbon (20–60 ppm, aliphatic) spectra are consistent with the lactam (closed-ring) form of the molecule. The ion at m/z 304 in the mass spectrum (ESI+) of (S)-4-isobutyl-1-(2,3,4,5-tetrahydroxy-tetrahydro-pyran-2-ylmethyl)-pyrrolidin-2-one arises from the protonated molecule. The mass of m/z 303 is consistent with the formula for (S)-4-isobutyl-1-(2,3,4,5-tetrahydroxy-tetrahydro-pyran-2-ylmethyl)-pyrrolidin-2-one, $C_{14}H_{25}NO_6$. The product ion spectrum is consistent with the proposed structure.

EXAMPLE 4

(S)-4-Isobutyl-1-(2,3,4,5-tetrahydroxy-tetrahydro-pyran-2-ylmethyl)-pyrrolidin-2-one Isolated (S)-4-isobutyl-1-(2,3,4,5-tetrahydroxy-tetrahydro-pyran-2-ylmethyl)-pyrrolidin-2-one, Lot P was 76% pure by HPLC area normalization. The relative response factor determined for (S)-4-isobutyl-1-(2,3,4,5-tetrahydroxy-tetrahydro-pyran-2-ylmethyl)-pyrrolidin-2-one versus pregabalin in the method is 30.6. Both anomeric protons are missing from the proton spectrum, and a nonproton bearing carbon at 98.3 ppm is observed in the $^{13}C$ spectrum. In the carbon spectrum, the profile of signals in the lyxose moiety (98.3, 72.1, 73.6, 69.5, and 61.9 for $C_1$–$C_5$, respectively) is consistent with the β-anomer (pyranose form) (Breitmaier E., Voelter W., supra., 1990). The chemical shifts arising from the pregabalin moiety in the proton (0.7–3.6 ppm) and carbon (20–60 ppm, aliphatic) spectra are consistent with the lactam (closed-ring) form of the molecule. The ion at m/z 304 in the mass spectrum (ESI+) of (S)-4-isobutyl-1-(2,3,4,5-tetrahydroxy-tetrahydro-pyran-2-ylmethyl)-pyrrolidin-2-one arises from the protonated molecule. The mass of m/z 303 is consistent with the formula for (S)-4-isobutyl-1-(2,3,4,5-tetrahydroxy-tetrahydro-pyran-2-ylmethyl)-pyrrolidin-2-one, $C_{14}H_{25}NO_6$. The product ion spectrum is consistent with the proposed structure.

EXAMPLE 5

(S)-4-Isobutyl-1-(2,3,4,5-tetrahydroxy-tetrahydro-pyran-2-ylmethyl)-pyrrolidin-2-one (Conjugate X) and (S)-4-Isobutyl-1-(2,3,4,5-tetrahydroxy-tetrahydro-pyran-2-ylmethyl)-pyrrolidin-2-one Isolated (S)-4-isobutyl-1-(2,3,4,5-tetrahydroxy-tetrahydro-pyran-2-ylmethyl)-pyrrolidin-2-one and (S)-4-isobutyl-1-(2,3,4-trihydroxy-5-hydroxymethyl-tetrahydro-furan-2-ylmethyl)-pyrrolidin-2-one in a 3:1 mixture using a modified HPLC method (see FIG. 3 for conditions). In the method for pregabalin capsules, the two compounds coelute along with (S)-4-isobutyl-1-(2,3,4,5-tetrahydroxy-tetrahydro-pyran-2-ylmethyl)-pyrrolidin-2-one. The relative response factor for (S)-4-isobutyl-1-(2,3,4,5-tetrahydroxy-tetrahydro-pyran-2-ylmethyl)-pyrrolidin-2-one and (S)-4-isobutyl-1-(2,3,4-trihydroxy-5-hydroxymethyl-tetrahydro-furan-2-ylmethyl)-pyrrolidin-2-one (3:1 mixture) versus pregabalin in this method is 30.2. No anomeric protons are observed in the proton spectrum, and nonproton bearing carbons at 98.6 and 101.5 ppm are observed in the $^{13}C$ spectrum. The profile of carbon signals in the arabinosyl moiety of (S)-4-isobutyl-1-(2,3,4,5-tetrahydroxy-tetrahydro-pyran-2-ylmethyl)-pyrrolidin-2-one (98.6, 69.1, 69.5, 69.0, and 63.5 ppm for $C_1$–$C_5$, respectively) is consistent with the β-pyranose form. The profile for the arabinosyl moiety of (S)-4-isobutyl-1-(2,3,4-trihydroxy-5-hydroxymethyl-tetrahydro-furan-2-ylmethyl)-pyrrolidin-2-one (101.5, 77.0, 74.3, 80.5, and 62.4 ppm for $C_1$–$C_5$, respectively) is consistent with the β-furanose form (Breitmaier E., Voelter W., supra., 1990). The chemical shifts arising from the pregabalin moiety in the proton (0.7–3.6 ppm) and carbon (20–60 ppm, aliphatic) spectra are consistent with the lactam (closed-ring) form of the molecule. The ion at m/z 304 in the mass spectra (ESI+) of (S)-4-isobutyl-1-(2,3,4,5-tetrahydroxy-tetrahydro-pyran-2-ylmethyl)-pyrrolidin-2-one and (S)-4-isobutyl-1-(2,3,4-trihydroxy-5-hydroxymethyl-tetrahydro-furan-2-ylmethyl)-pyrrolidin-2-one arise from the protonated molecule. The mass of m/z 303 is consistent with the formula for both (S)-4-isobutyl-1-(2,3,4,5-tetrahydroxy-tetrahydro-pyran-2-ylmethyl)-pyrrolidin-2-one and (S)-4-isobutyl-1-(2,3,4-trihydroxy-5-hydroxymethyl-tetrahydro-furan-2-ylmethyl)-pyrrolidin-2-one, $C_{14}H_{25}NO_6$. The product ion spectrum is consistent with the proposed structures.

Pregabalin undergoes a Maillard reaction to form conjugates with lactose in formulated product. Seven of these conjugates, which exist in the lactam form of the pregabalin moiety, were generated in milligram to gram quantities by heating pregabalin in the presence of lactose. The compounds were then isolated by preparative liquid chromatography. The assigned structures of the isolated lactose-lactam conjugates were consistent with the NMR and mass spectrometry data. Of the seven compounds identified, one compound ((S)-1-[3,4-dihydroxy-6-hydroxymethyl-5-(3,4,5-trihydroxy-6-hydroxymethyl-tetrahydro-pyran-2-yloxy)-tetrahydro-pyran-2-yl]-4-isobutyl-pyrrolidin-2-one) is the Maillard reaction product of pregabalin and lactose. The lactose used in the reaction was originally the α-lactose. However, upon dissolution in the above reaction conditions, the lactose rapidly equilibrates between the α and β forms. The conjugate (S)-1-[3,4-dihydroxy-6-hydroxymethyl-5-(3,4,5-trihydroxy-6-hydroxymethyl-tetrahydro-pyran-2-yloxy)-tetrahydro-pyran-2-yl]-4-isobutyl-pyrrolidin-2-one is the β-anomer. Two of the compounds ((S)-4-isobutyl-1-[2,3,5-trihydroxy-4-(3,4,5-trihydroxy-6-hydroxymethyl-tetrahydro-pyran-2-yloxy)-tetrahydro-pyran-2-ylmethyl]-pyrrolidin-2-one and (S)-1-[2,3-dihydroxy-5-hydroxymethyl-4-(3,4,5-trihydroxy-6-hydroxymethyl-tetrahydro-pyran-2-yloxy)-tetrahydro-furan-2-ylmethyl]-4-isobutyl-pyrrolidin-2-one) result from the Amadori rearrangement of (S)-1-[3,4-dihydroxy-6-hydroxymethyl-5-(3,4,5-trihydroxy-6-hydroxymethyl-tetrahydro-pyran-2-yloxy)-tetrahydro-pyran-2-yl]-4-isobutyl-pyrrolidin-2-one. One product is the β-furanose form ((S)-1-[2,3-dihydroxy-5-hydroxymethyl-4-(3,4,5-trihydroxy-6-hydroxymethyl-tetrahydro-pyran-2-yloxy)-tetrahydro-furan-2-ylmethyl]-4-isobutyl-pyrrolidin-2-one), and the other is the β-pyranose form ((S)-4-isobutyl-1-[2,3,5-trihydroxy-4-(3,4,5-trihydroxy-6-hydroxymethyl-tetrahydro-pyran-2-yloxy)-tetrahydro-pyran-2-ylmethyl]-pyrrolidin-2-one). The remaining four conjugates are monosaccharides, resulting from the Maillard reaction/Amadori rearrangement of pregabalin with either the galactose ((S)-4-isobutyl-1-(2,3,4,5-tetrahydroxy-tetrahydro-pyran-2-ylmethyl)-pyrrolidin-2-one and (S)-4-isobutyl-1-(2,3,4,5-tetrahydroxy-tetrahydro-pyran-2-ylmethyl)-pyrrolidin-2-one) or glucose ((S)-4-isobutyl-1-(2,3,4,5-tetrahydroxy-tetrahydro-pyran-2-ylmethyl)-pyrrolidin-2-one and (S)-4-isobutyl-1-(2,3,4-trihydroxy-5-hydroxymethyl-tetrahydro-furan-2-ylmethyl)-pyrrolidin-2-one) moiety of lactose. In separate experiments, pregabalin (300 mg) was reacted in 5 mL $H_2O$ (adjusted to pH 11 with KOH) at 80° C. with glucose (600 mg) and galactose (600 mg). In the glucose reaction, a 3:1 mixture of (S)-4-isobutyl-1-(2,3,4,5-tetrahydroxy-tetrahydro-pyran- 2-ylmethyl)-pyrrolidin-2-one and (S)-4-isobutyl-1-(2,3,4-trihydroxy-5-hydroxymethyl-tetrahydro-furan-2-ylmethyl)-pyrrolidin-2-one resulted. In the galactose reaction, a 5:1 mixture of (S)-4-isobutyl-1-(2,3,4,5-tetrahydroxy-tetrahydro-pyran-2-ylmethyl)-pyrrolidin-2- one and (S)-4-isobutyl-1-(2,3,4,5-tetrahydroxy-tetrahydro-pyran-2-ylmethyl)-pyrrolidin-2-one resulted. These experimental results support the structural assignments of the monosaccharide conjugates.

EXAMPLE 6

| Tablet Formulation | |
|---|---|
| Ingredient | Amount (mg) |
| Compound of Example 1 | 25 |
| Lactose | 50 |
| Cornstarch (for mix) | 10 |
| Cornstarch (paste) | 10 |
| Magnesium stearate (1%) | 5 |
| Total | 100 |

The compound of Example 1, lactose, and cornstarch (for mix) are blended to uniformity. The cornstarch (for paste) is suspended in 200 mL of water and heated with stirring to form a paste. The paste is used to granulate the mixed powders. The wet granules are passed through a No. 8 hand screen and dried at 80° C. The dry granules are lubricated with the 1% magnesium stearate and pressed into a tablet.

EXAMPLE 7

Coated Tablets

The tablets of Example 6 are coated in a customary manner with a coating of sucrose, potato starch, talc, tragacanth, and colorant.

EXAMPLE 8

Injection Vials

The pH of a solution of 500 g of the compound of Example 1 and 5 g of disodium hydrogen phosphate is adjusted to pH 6.5 in 3 L of double-distilled water using 2 M hydrochloric acid. The solution is sterile filtered. and the filtrate is filled into injection vials, lyophilized under sterile conditions, and aseptically sealed. Each injection vial contains 25 mg of the compound of Example 1.

EXAMPLE 9

Suppositories

A mixture of 25 g of the compound of Example 1, 100 g of soya lecithin, and 1400 g of cocoa butter is fused, poured into molds, and allowed to cool. Each suppository contains 25 mg of the compound of Example 1.

EXAMPLE 10

Solution

A solution is prepared from 1 g of the compound of Example 1, 9.38 g of $NaH_2PO_4.2H_2O$, 28.48 g of $Na_2HPO_4.12H_2O$, and 0.2 g benzalkonium chloride in 940 mL of double-distilled water. The pH of the solution is adjusted to pH 6.8 using 2 M hydrochloric acid. The solution is diluted to 1.0 L with double-distilled water, and sterilized by irradiation. A 25 mL volume of the solution contains 25 mg of the compound of Example 1.

EXAMPLE 11

Ointment 500 mg of the compound of Example 1 is mixed with 99.5 g of petroleum jelly under aseptic conditions. A 5 g portion of the ointment contains 25 mg of the compound of Example 1.

EXAMPLE 12

Capsules 2 kg of the compound of Example 1 are filled into hard gelatin capsules in a customary manner such that each capsule contains 25 mg of the invention compound.

EXAMPLE 13

Ampoules

A solution of 2.5 kg of the compound of Example 1 is dissolved in 60 L of double-distilled water. The solution is sterile filtered, and the filtrate is filled into ampoules. The ampoules are lyophilized under sterile conditions and aseptically sealed. Each ampoule contains 25 mg of the compound of Example 1.

While the forms of the invention exemplified herein such as, for exmple, the named species or the recitation of treatment of pain or Parkinson's disease constitute preferred embodiments of the invention, many other preferred embodiments are possible. It is not intended that the preferred embodiments of the compounds or preferred methods of use of said compounds, recited above should, in any manner, limit or restrict the invention from the full scope claimed herein.

TABLE 1

| Preparative HPLC Conditions | |
|---|---|
| Operating Parameter | Description |
| Column: | Dynamax, C18, 8 μm, 100 mm guard + 250 × 41 mm |
| Mobile Phase: | 15:10:75 Acetonitrile:Methanol:0.1% formic acid ((S)-1-[3,4-Dihydroxy-6-hydroxymethyl-5-(3,4,5-trihydroxy-6-hydroxymethyl-tetrahydro-pyran-2-yloxy)-tetrahydro-pyran-2-yl]-4-isobutyl-pyrrolidin-2-one, (S)-4-Isobutyl-1-[2,3,5-trihydroxy-4-(3,4,5-trihydroxy-6-hydroxymethyl-tetrahydro-pyran-2-yloxy)-tetrahydro-pyran-2-ylmethyl]-pyrrolidin-2-one, and (S)-1-[2,3-Dihydroxy-5-hydroxymethyl-4-(3,4,5-trihydroxy-6-hydroxymethyl-tetrahydro-pyran-2-yloxy)-tetrahydro-furan-2-ylmethyl]-4-isobutyl-pyrrolidin-2-one isolation) 550:350:100:1 $H_2O$:MeOH:$CH_3CN$:pH 7 buffer ((S)-4-Isobutyl-1-(2,3,4,5-tetrahydroxy-tetrahydro-pyran-2-ylmethyl)-pyrrolidin-2-one and (S)-4-Isobutyl-1-(2,3,4,5-tetrahydroxy-tetrahydro-pyran-2-ylmethyl)-pyrrolidin-2-one CONJUGATE C) 850:150:1 $H_2O$:$CH_3CN$:pH 7 buffer ((S)-4-Isobutyl-1-(2,3,4,5-tetrahydroxy-tetrahydro-pyran-2-ylmethyl)-pyrrolidin-2-one CONJUGATE X and (S)-4-Isobutyl-1-(2,3,4-trihydroxy-5-hydroxymethyl-tetrahydro-furan-2-ylmethyl)-pyrrolidin-2-one CONJUGATE Y) |
| Column Temperature: | Ambient |
| Detector Wavelength: | None used |
| Injection Volume: | 20 mL |
| Flow Rate: | 25 mL/min |
| Run Time: | 60 min |

TABLE 2

Relative Response Factor of Conjugates Versus Pregabalin

| Conjugate (from Scheme 3) | Relative Response Factor[a] |
|---|---|
| 1 | 15.9 |
| 5[b] | 20.2 |
| 4[b] | 20.2 |
| 2 | 28.1 |
| 3[b] | 30.6 |
| 6[b] | 30.2 |
| 7 | 30.2 |

[a]Using the Specification and Test Method (RTD-1008-CH1-3)
[b]Isomers determined as a 3:1 mixture

What is claimed is:

1. A compound selected from:
   (S)-1-[3,4-Dihydroxy-6-hydroxymethyl-5-(3,4,5-trihydroxymethyl tetrahydro-pyran-2-yloxy)-tetrahydro-pyran-2-yl]-4-isobutyl-pyrrolidin 2-one;
   (S)-4-Isobutyl-1-(2,3,4,5-tetrahydroxy-tetrahydro-pyran 2-ylmethyl)-pyrrolidin-2-one;
   (S)-1-[2,3-Dihydroxy-5-hydroxymethyl-4-(3,4,5-trihydroxy-6 hydroxymethyl-tetrahydro-pyran-2-yloxy)-tetrahydro-furan-2-ylmethyl]-4-isobutyl-pyrrolidin-2-one;
   (S)-4-Isobutyl-1-[2,3,5-trihydroxy-4-(3,4,5-trihydroxy 6-hydroxymethyl-tetrahydro-pyran-2-yloxy)-tetrahydro-pyran-2-ylmethyl]-pyrrolidin-2-one; and
   (S)-4-Isobutyl-1-(2,3,4-trihydroxy-5-hydroxymethyl-tetrahydro furan-2-ylmethyl)-pyrrolidin-2-one.

2. A compound according to claim 1 selected from:

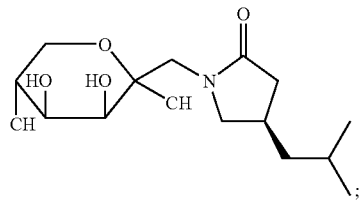

3. A pharmaceutical composition comprising at least one compound of claim 1 and a pharmaceutically acceptable carrier, excipient, or diluent thereof.

4. A compound according to claim 1 where the compound is in isolated form.

5. A compound having the formula

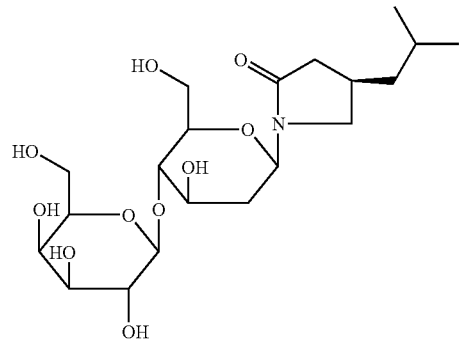

* * * * *